(12) United States Patent
Wilson

(10) Patent No.: US 8,118,879 B2
(45) Date of Patent: *Feb. 21, 2012

(54) PROSTHETIC FOOT WITH FLEXIBLE ANKLE PORTION

(76) Inventor: Michael T. Wilson, Missouri City, TX (US)

(*) Notice: Subject to any disclaimer, the term of this patent is extended or adjusted under 35 U.S.C. 154(b) by 145 days.

This patent is subject to a terminal disclaimer.

(21) Appl. No.: 12/048,512

(22) Filed: Mar. 14, 2008

(65) Prior Publication Data

US 2009/0234463 A1 Sep. 17, 2009

(51) Int. Cl.
*A61F 2/66* (2006.01)
*A61F 2/68* (2006.01)
(52) U.S. Cl. ............................ 623/55; 623/52
(58) Field of Classification Search .............. 623/48, 623/52, 53, 55, 47, 49–51, 54
See application file for complete search history.

(56) References Cited

U.S. PATENT DOCUMENTS

| | | | |
|---|---|---|---|
| 0,409,311 A | 8/1889 | Snyder | |
| 0,419,019 A | 1/1890 | Koble | |
| 0,766,686 A | 8/1904 | Gault | |
| 1,071,230 A | 8/1913 | Hanger | |
| 1,294,632 A | 2/1919 | Dickson | |
| 2,066,599 A * | 1/1937 | Willett | 623/49 |
| 2,450,728 A | 10/1948 | Havens | |
| 2,594,752 A | 4/1952 | Fahlstrom | |
| 2,605,475 A | 8/1952 | Burger et al. | |
| 2,620,485 A | 12/1952 | Greissinger | |
| 2,731,645 A | 1/1956 | Woodall | |
| 2,745,108 A | 5/1956 | Withers | |
| 3,196,463 A | 7/1965 | Farneth | |
| 3,480,972 A | 12/1969 | Prahl | |
| 3,940,804 A | 3/1976 | Benton et al. | |
| 3,945,737 A | 3/1976 | Herbenar | |
| 3,982,278 A | 9/1976 | May | |
| 4,134,159 A | 1/1979 | Wilson | |
| 4,328,594 A | 5/1982 | Campbell et al. | |
| 4,387,472 A | 6/1983 | Wilson | |
| 4,446,580 A | 5/1984 | Furuya et al. | |
| 4,461,045 A | 7/1984 | Shorter et al. | |
| 4,463,459 A | 8/1984 | Shorter et al. | |
| 4,547,913 A | 10/1985 | Phillips | |
| 4,645,509 A | 2/1987 | Poggi et al. | |

(Continued)

FOREIGN PATENT DOCUMENTS

AT 0196553 3/1958

(Continued)

OTHER PUBLICATIONS

Merriam Webster Online Dictionoary Definition, Monolithic, Accessed Feb. 23, 2011.*

(Continued)

*Primary Examiner* — David Isabella
*Assistant Examiner* — Marcia Hoffman
(74) *Attorney, Agent, or Firm* — Conley Rose, P.C.

(57) ABSTRACT

A keel for a prosthetic foot comprises a unitary keel body having a longitudinal axis and a length L. The keel body includes a forefoot portion, a heel portion, and an ankle portion extending therebetween. In addition, the keel comprises a first bumper disposed in a first capture cavity in the ankle portion. The first bumper has a central axis that is substantially perpendicular to the longitudinal axis of the keel body in top view.

22 Claims, 7 Drawing Sheets

U.S. PATENT DOCUMENTS

| | | | |
|---|---|---|---|
| 4,652,266 A * | 3/1987 | Truesdell | 623/55 |
| 4,721,510 A | 1/1988 | Cooper et al. | |
| 4,764,172 A | 8/1988 | McCoy | |
| 4,822,363 A | 4/1989 | Phillips | |
| 4,865,612 A | 9/1989 | Arbogast et al. | |
| 4,889,458 A | 12/1989 | Taylor | |
| 4,892,554 A | 1/1990 | Robinson | |
| 4,969,911 A | 11/1990 | Greene | |
| 5,030,239 A | 7/1991 | Copes | |
| 5,037,444 A | 8/1991 | Phillips | |
| 5,112,356 A | 5/1992 | Harris et al. | |
| 5,116,384 A | 5/1992 | Wilson et al. | |
| 5,156,632 A | 10/1992 | Wellershaus | |
| 5,158,570 A | 10/1992 | Schey et al. | |
| 5,219,364 A | 6/1993 | Lloyd | |
| 5,258,038 A | 11/1993 | Robinson et al. | |
| 5,376,140 A | 12/1994 | Ryan | |
| 5,443,527 A | 8/1995 | Wilson | |
| 5,482,513 A | 1/1996 | Wilson | |
| 5,545,234 A | 8/1996 | Collier, Jr. | |
| 5,549,714 A | 8/1996 | Phillips | |
| 5,695,526 A | 12/1997 | Wilson | |
| 5,728,171 A | 3/1998 | Bryant, Jr. et al. | |
| 5,769,896 A * | 6/1998 | Rosendahl et al. | 623/49 |
| 5,800,570 A | 9/1998 | Collier | |
| 5,993,487 A * | 11/1999 | Skardoutos et al. | 623/38 |
| 6,165,177 A | 12/2000 | Wilson et al. | |
| 6,228,124 B1 | 5/2001 | Slemker et al. | |
| 6,231,618 B1 | 5/2001 | Schall et al. | |
| 6,290,730 B1 * | 9/2001 | Pitkin et al. | 623/49 |
| 6,511,514 B1 | 1/2003 | Wilson | |
| 6,572,659 B1 | 6/2003 | Ryan | |
| 6,663,673 B2 * | 12/2003 | Christensen | 623/56 |
| 6,712,860 B2 | 3/2004 | Rubie et al. | |
| 6,719,807 B2 | 4/2004 | Harris | |
| 2002/0082713 A1 | 6/2002 | Townsend et al. | |
| 2004/0068327 A1 | 4/2004 | Christensen | |
| 2004/0225376 A1 | 11/2004 | Townsend et al. | |
| 2005/0033450 A1 | 2/2005 | Christensen | |
| 2005/0033451 A1 | 2/2005 | Aigner et al. | |
| 2005/0060045 A1 | 3/2005 | Smith | |
| 2005/0071018 A1 | 3/2005 | Phillips et al. | |
| 2005/0085926 A1 | 4/2005 | Christensen | |
| 2005/0234563 A1 * | 10/2005 | Phillips | 623/55 |
| 2005/0261783 A1 * | 11/2005 | Geilman et al. | 623/52 |
| 2006/0069450 A1 * | 3/2006 | McCarvill et al. | 623/55 |
| 2007/0250178 A1 | 10/2007 | Wilson | |

FOREIGN PATENT DOCUMENTS

| | | |
|---|---|---|
| DE | 814025 | 9/1951 |
| DE | 2241971 | 3/1974 |
| DE | 9104823 | 6/1991 |
| EP | 224373 | 6/1987 |
| EP | 0280004 | 8/1988 |
| FR | 0481770 | 10/1916 |
| FR | 1233031 | 10/1960 |
| FR | 504342 | 6/1990 |
| FR | 2640499 | 6/1990 |
| GB | 227290 | 1/1925 |
| GB | 621576 | 4/1949 |
| GB | 731223 | 6/1955 |
| GB | 2070439 | 9/1981 |
| GB | 2092451 | 8/1982 |
| SU | 169349 | 11/1951 |
| SU | 1424831 | 11/1951 |
| SU | 1391643 | 4/1988 |
| SU | 1409258 | 7/1988 |
| SU | 1747062 | 7/1992 |
| WO | 8400681 | 3/1984 |
| WO | 8800815 | 2/1988 |
| WO | 8806431 | 9/1988 |

OTHER PUBLICATIONS

SPS Pamphlet, with description of prosthetic foot; (1 p.).
APC Duroflex (TM) pages, with descriptions of prosthetic feet; (1 p.).
APC Duroflex (TM) Brochure, description of prosthetic foot; (4 p.).
Flex-Foot, Inc. flyers entitled, "Something Revolutionary is in the Air", "adjust the foot, not the lifestyle", "Engineered for the Long Run", Simply Precise, engineered Flexibility, Designed for a Growing Market, Amputee Profile (Mary J. Gardner), "Amputee Profile (D. Broome)", and Flex-Foot, Inc., Newsletter, Issue No. 4, 1992; (20 p.).
Otto Bock Flyer, "1M1—Otto Bock Multiaxial Foot"; (1982) (4 p.).
Campbell-Childs, Inc. brochure and flyer (14th anniversary—1979-1993), entitled "The all New 'Sportsman' S.A.F.E. II", (12 p.).
Devcon instruction sheet #7041 on "Flexane Urethane"; Jul. 1992; (2 p.).
Boston Gear catalog, Self-Aligning Bearings, p. D68; (1 p.).
Hosmer brochure; The Quantum Foot; (5 p.).
Campbell-Childs, Inc. Stationary attachment Flexible Endoskelton II Mailer, Jul. 1989 (2 p.).
Campbell-Childs, Inc. S.A.F.E. Prosthetic Foot Catalog; (8 p.).
United States Manufacturing Company—Multiplex Brochure; "Now More Flexibility for Amputees Who Use the Multiplex"; 1988; (1 p.).
The Ohio Willow Wood Co., "Step into the Future with the Carbon Copy II Energy Storing Foot"; (4 p.).
Footnotes (Flex-Foot)—Mailer, Mar. 1989; (4 p.
Flex-Foot, Inc.—Price List (Sep. 1, 1989); (8 p.).
Office Action dated Aug. 14, 2008 for U.S. Appl. No. 11/264,113 (20 p.).
Response to Office Action dated Aug. 14, 2008 for U.S. Appl. No. 11/264,113 (15 p.).
Office Action dated Feb. 18, 2009 for U.S. Appl. No. 11/264,113 (9 p.).
Response to Office Action dated Feb. 18, 2009 for U.S. Appl. No. 11/264,113 (16 p.).
Interview Summary dated Aug. 17, 2009 for U.S. Appl. No. 11/264,113 (2 p.).
Response to Interview Summary dated Aug. 17, 2009 for U.S. Appl. No. 11/264,113 (3 p.).
Final Office Action dated Aug. 20, 2009 for U.S. Appl. No. 11/264,113 (10 p.).
Response to Final Office Action dated Aug. 20, 2009 for U.S. Appl. No. 11/264,113 (15 p.).
Advisory Action dated Dec. 16, 2009 for U.S. Appl. No. 11/264,113 (3 p.).
Office Action dated Jan. 27, 2010 for U.S. Appl. No. 11/264,113 (18 p.).
Response to Office Action dated Jan. 27, 2010 for U.S. Appl. No. 11/264,113 (17 p.).

* cited by examiner

PROSTHETIC FOOT WITH FLEXIBLE ANKLE PORTION

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

Field of the Invention

The present invention relates generally to a prosthetic foot. More particularly, the present invention relates to a prosthetic foot with a flexible ankle portion to simulate the flexibility and flexion normally provided by an anatomical foot and ankle.

Background of the Invention

A useful prosthesis must at least partially simulate the operation and motion of an anatomical foot. In addition, for Syme amputees (e.g., amputees who have sustained an ankle disarticulation), a useful prosthesis must simulate the operation, flexion, and motion of an anatomical ankle.

An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement of the ball of the foot upward and downward, respectively, with respect to the heel. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

Some prosthetic feet that include a distinct prosthetic ankle capable of complicated motion (e.g., motion around two or three axes). In particular, such prostheses may be useful for Syme amputees since the inclusion of a prosthetic ankle may simulate the operation, flexion, and motion normally provided by an anatomical ankle. However, inclusion of a prosthetic ankle may add bulk and additional weight to the prosthesis. The additional weight may result in a prosthesis that is too heavy for some patients, such as geriatric patients, very young patients, or other patients who suffer some degree of muscular weakness.

Moreover, although some flexibility may be desirable, a prosthetic foot must also provide a secure and relatively rigid means for coupling the prosthetic foot to the amputee. Some conventional prosthetic feet may provide a rigid metal plate that is bolted to the prosthetic foot to couple the prosthetic foot to the amputee. However, the use of a metal plate adds bulk, tends to reduce the flexibility of the prosthetic foot, as well as create stress concentrations around the bolt attachment points of the prosthetic foot. Concentration of stresses proximal the areas where the prosthetic foot flexes may lead to premature weakening, cracking, or breaking of the prosthetic foot.

In addition, it is desirable for a prosthetic foot to provide a spring effect during use (e.g., be capable of absorbing, storing, and releasing energy). At a minimum, the prosthesis should store enough energy to return itself to a relaxed, unflexed position when external forces are removed. Such a spring effect may be accomplished by the inclusion of energy storing components such as coil springs. However, such energy-storing components may significantly increase the weight of the prosthesis.

Finally, it is necessary that a prosthetic foot be strong enough to support its wearer and durable enough to withstand the stresses of repeated stepping motions over long periods of time. Some conventional prostheses may be designed for maximize strength, at the cost of added bulk and weight, making them unsuitable for some amputees.

Thus, there remains a need to develop methods and apparatus for improved foot prostheses which overcome some of the foregoing difficulties while providing more advantageous overall results.

BRIEF SUMMARY OF SOME OF THE PREFERRED EMBODIMENTS

These and other needs in the art are addressed in one embodiment by a keel for a prosthetic foot. In an embodiment, the keel comprises a unitary keel body having a longitudinal axis and a length L. The keel body includes a forefoot portion, a heel portion, and an ankle portion extending therebetween. In addition, the keel comprises a first bumper disposed in a first capture cavity in the ankle portion. The first bumper has a central axis that is substantially perpendicular to the longitudinal axis of the keel body in top view.

Theses and other needs in the art are addressed in another embodiment by a prosthetic foot. In an embodiment, the prosthetic foot comprises a unitary keel body having a longitudinal axis and a length L. The keel body includes a forefoot portion having a toe end, a ankle portion including an integral semi-spherical dome, and a heel portion having a heel end. In addition, the prosthetic foot comprises a rear bumper disposed in a capture cavity between the dome and the heel end. The rear bumper has a central axis that is substantially perpendicular to the longitudinal axis of the keel body in top view.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more detailed description of the preferred embodiment of the present invention, reference will now be made to the accompanying drawings, wherein.

DETAILED DESCRIPTION OF THE INVENTION

Figure 1:
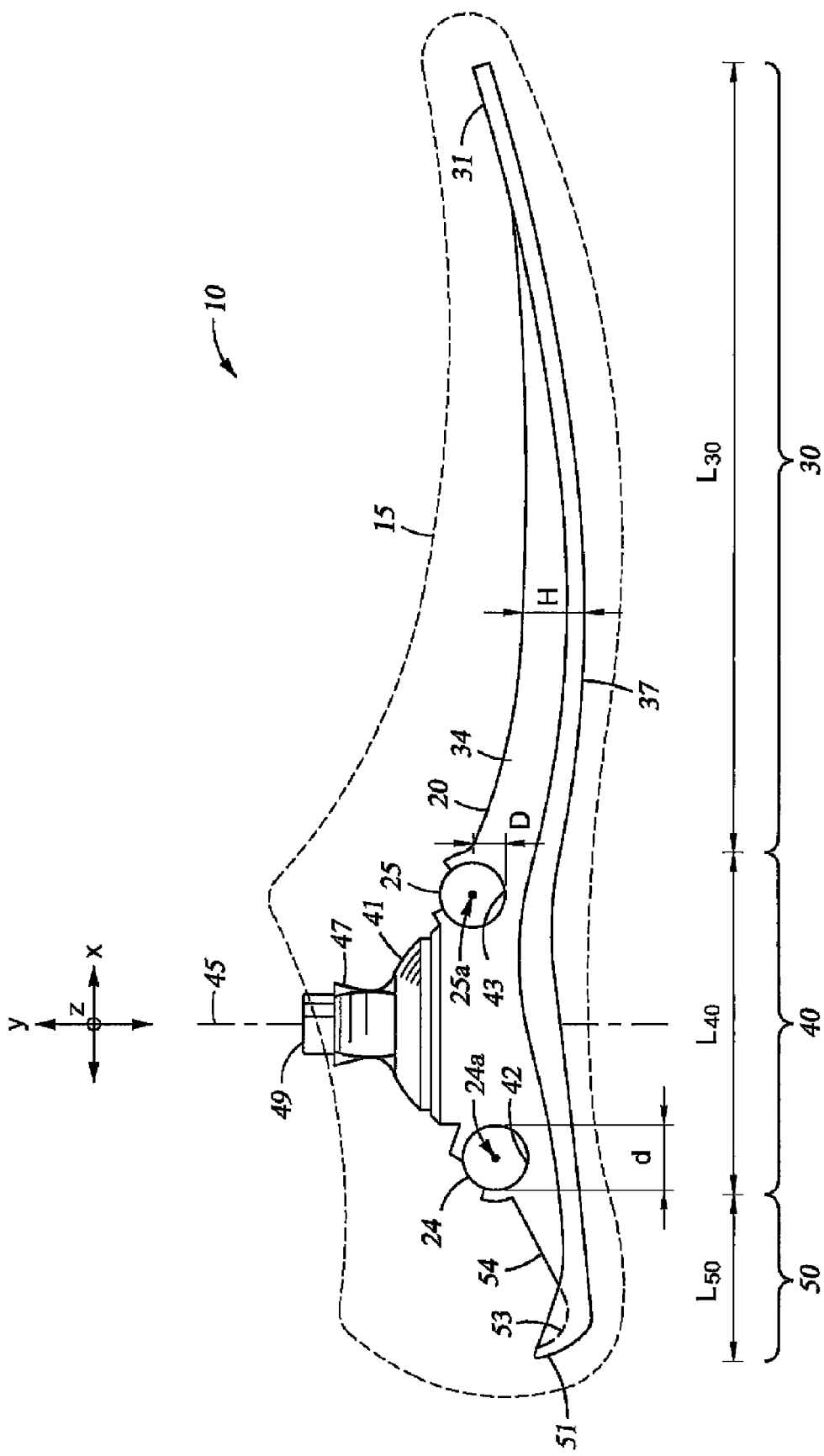
FIG. 1 is a side view of an embodiment of a prosthetic foot made in accordance with the principles described herein.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular system components. As one skilled in the art will appreciate, different persons may refer to a component by different names. This document does not intend to distinguish between components that differ in name but not function. The drawing figures are not necessarily to scale. Certain features of the invention may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices and connections.

For purposes of discussion, the x-, y-, and z-axes are shown in FIG. 1 and have been assigned as follows. The x-axis is perpendicular to the longitudinal axis of the leg and parallel to the longitudinal axis of the foot. Generally, inversion and eversion (e.g., the twisting of the foot about its longitudinal axis) may occur about the x-axis. The y-axis is parallel to the longitudinal axis of the leg. Generally, transverse rotation (rotation of the foot with respect to the longitudinal axis of the leg) may occur about the z-axis. The z-axis is perpendicular to the longitudinal axis of the leg and the longitudinal axis of the foot, generally passing through the lateral sides of the ankle. Generally, dorsiflexion and planiflexion (e.g., movement of the ball of the foot upward and downward, respectively) may occur about the z-axis. It is to be understood that the three axes (x-axis, y-axis, and z-axis) are orthogonal.

Figure 2:
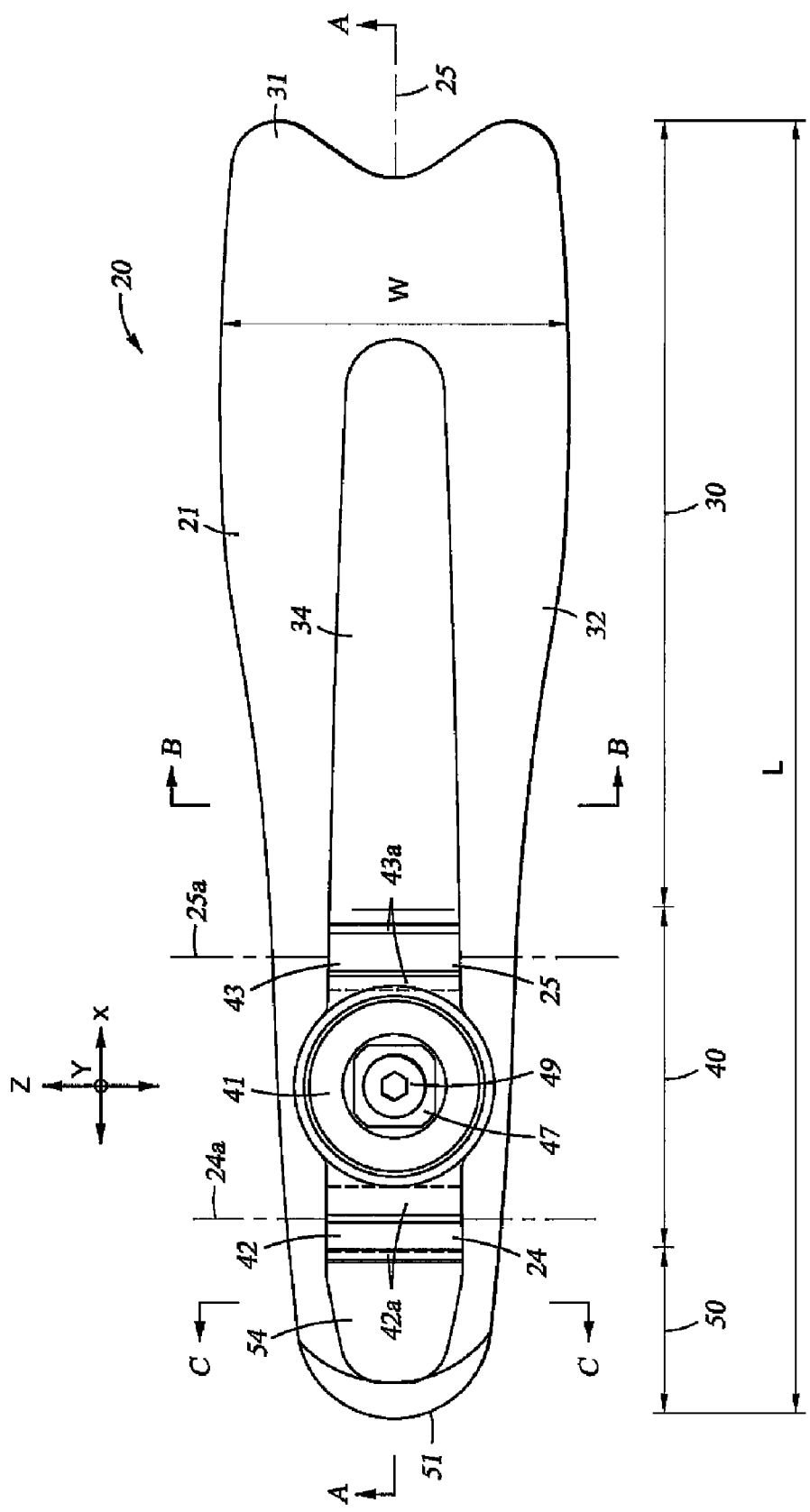
FIG. 2 is a top view of the keel of FIG. 1.
Figure 3:
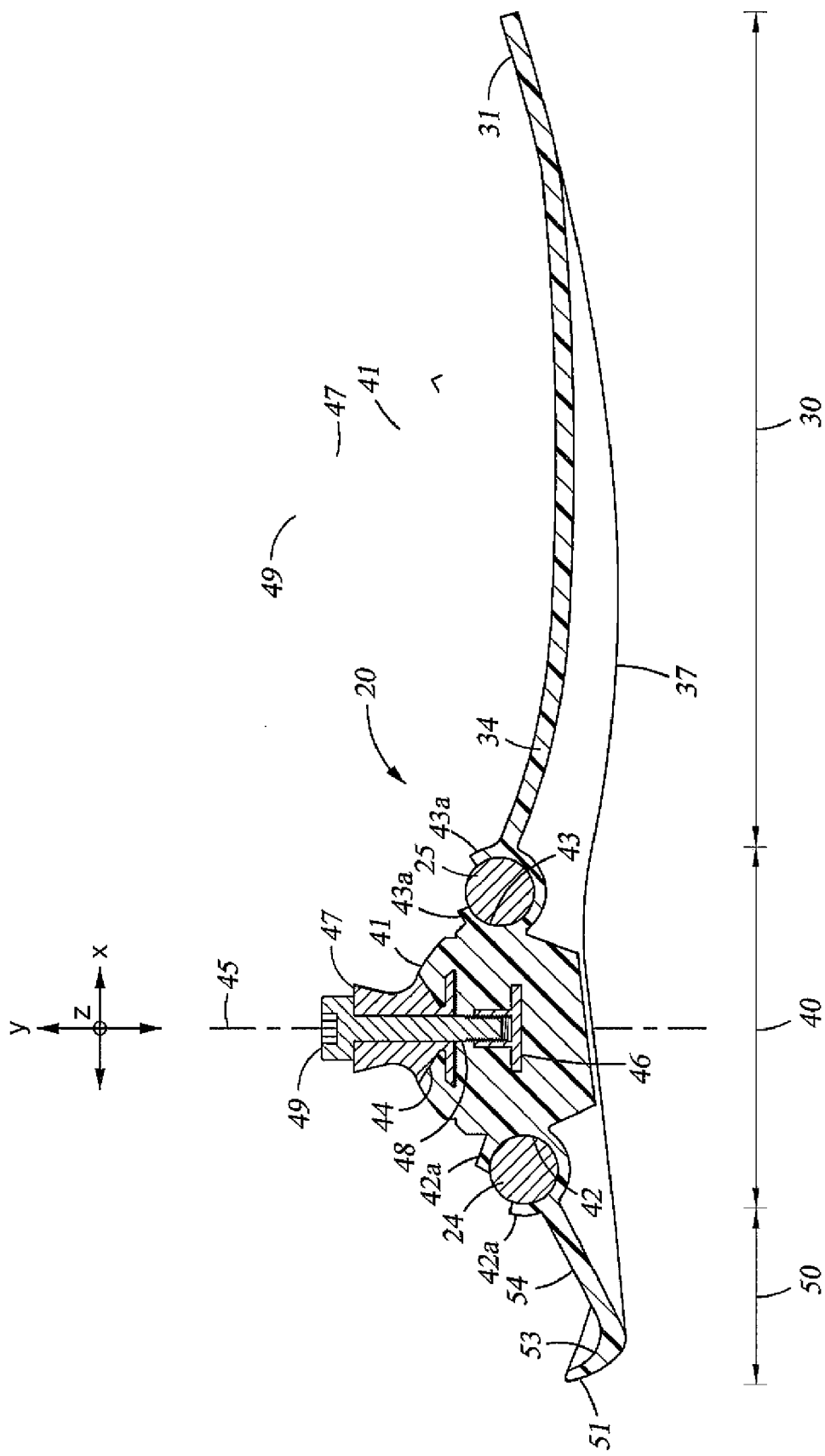
FIG. 3 is a cross-sectional view of the keel of FIG. 1 taken along line A-A of FIG. 2.

Referring now to FIGS. 1-3, an embodiment of a prosthetic foot 10 is shown. Foot 10 comprises a keel 20 and a cosmesis 15 (shown in phantom in FIG. 1). Cosmesis 15 substantially surrounds keel 20 and provides the external appearance of prosthetic foot 10. The cosmesis (e.g., cosmesis 15) is preferably made of foamed polyethylene and ethylene-vinyl acetate copolymer (EVA). In select embodiments, the inside of the cosmesis is formed of expanded polyethylene and the outside is formed of expanded EVA, which offers the potential for improved abrasion resistance. Together, keel 20 and cosmesis 15 closely replicate the structure and form of an anatomical foot, including the ankle joint.

Keel 20 comprises a keel body 21, a first or rear ankle bumper 24 coupled to keel body 21, and a second or front ankle bumper 25 coupled to keel body 21. Keel 20 extends along a longitudinal axis 25 from a heel end 51 to a toe end 31. Keel 20 has a length L measured between toe end 31 and heel end 51 along longitudinal axis 25 (generally parallel to the x-axis), a width W measured between the lateral sides of keel 20 perpendicular to longitudinal axis 25 (generally parallel to the z-axis), and a height H measured from the bottom surface of keel 20 to the uppermost surface of keel 20 perpendicular to longitudinal axis 25 (generally parallel to the y-axis). In general, the length L, width W, and height H of keel 20 may be varied depending on a variety of factors including, without limitation, the age of the amputee, the expected activities of the amputee, the size and weight of the amputee, or combinations thereof. For most applications, the length L of keel 20 is preferably between 20 and 35 cm, and more preferably between 22 and 30 cm. Similar to an anatomical foot, the height H and the width W of keel 20 vary along the length L of keel 20. For instance, the width W of keel 20 at toe end 31 is greater than the width W of keel 20 at heel end 51.

In general, the keel body (e.g., keel body 21) may comprise any suitable material(s) including, without limitation, polymers (e.g., plastic), composites (e.g., carbon fiber and epoxy composite), or combinations thereof. More specifically, the keel body preferably comprises a rigid or semi-rigid material with sufficient strength to bear the weight and loads applied by the patient. However, to minimize the bulk and weight of the keel (e.g., keel 20) and the prosthetic foot (e.g., prosthetic foot 10), the keel body also preferably comprises a relatively lightweight material. Further, to more closely simulate the flexibility and flexion of an anatomical foot, the keel body preferably comprises a resilient material capable of flexing under loads, and capable of returning to its unflexed state upon removal of any applied loads. Exemplary materials suitable for the keel body include polypropylene or a polypropylene-polyethylene blend preferably employing a low molecular weight polyethylene. Without being limited by this or any particular theory, in those embodiments where the keel body comprises a polypropylene-polyethylene blend, the greater the percentage of polyethylene (by weight), the greater the flexibility and softness of the keel body, whereas the greater the polypropylene, the greater the stiffness and resiliency of the keel body. In general, the keel body may be formed by any suitable means including, without limitation, molding, casting, machining, or combinations thereof. In embodiments where the keel body (e.g., keel body 21) comprises a polymer such as polypropylene or a polypropylene-polyethylene blend, the keel body is preferably formed by injection molding or compression molding.

Referring still to FIGS. 1-3, keel body 21 may generally be divided into a forefoot portion 30, a heel portion 50, and a mid-foot or ankle portion 40 extending therebetween. As best shown in FIG. 1, forefoot portion 30 has a length $L_{30}$ that is about 50% to 65% of the length L of keel 20, ankle portion 40 has a length $L_{40}$ that is about 8% to 15% of the length L of keel 20, and heel portion 50 has a length $L_{50}$ that is about 10% to 20% of the length L of keel 20. In this embodiment, portions 30, 40, 50 of keel body 21 are integral, and thus, form a single-piece or unitary keel body 21.

Forefoot portion 30 includes a lower base 32 and a raised instep 34. Base 32 has a substantially flat toe end 31 and a roll contact 37. Raised instep 34 extends vertically from base 32 generally along longitudinal axis 25 from proximal toe end 31 to ankle portion 40. Roll contact 37 is generally convex and is disposed along the lower surface of base 32. Roll contact 37 generally represents the region about which forefoot portion 30 pivots as prosthetic foot 10 contacts the ground a normal forward or backward step. The actual location of roll contact 37 may vary depending on a variety of factors including, without limitation, the size of the amputee, the desired flexibility of foot 10, the expected activities of the amputee (e.g., walking, running, etc.), the age of the amputee, or combinations thereof. However, for most applications, roll contact 37 is preferably positioned between 30% and 50% of the length L of keel 20 from toe end 31 (50% to 70% of the length L from heel end 51), and more preferably between 35% and 45% of the length L of keel body 20 from the toe end 31 (45% to 55% of the length L from heel end 51).

Figure 4:
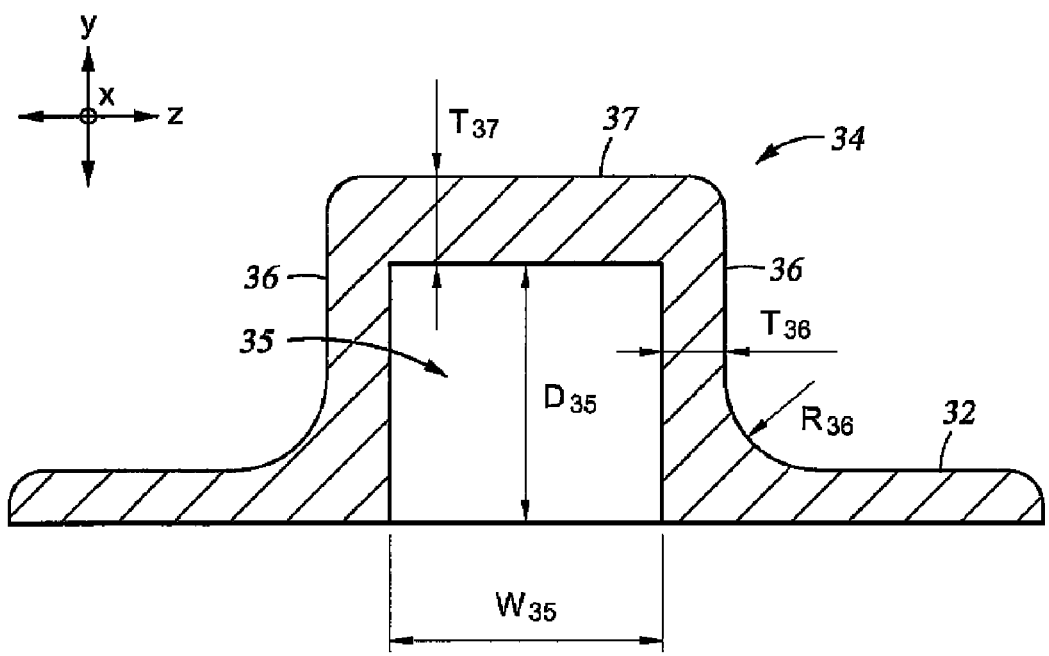
FIG. 4 is a cross-sectional view of the keel of FIG. 1 taken along line B-B of FIG. 2.

Referring now to FIG. 4, a cross-section of keel body 21 in forefoot portion 30 is shown. Raised instep 34 includes generally vertical sidewalls 36 and a generally horizontal upper wall 37 extending between sidewalls 36. Sidewalls 36 are smoothly blended into base 32 with a transition radius $R_{36}$. To eliminate share edges and the potential for stress concentrations, transition radius $R_{36}$ is preferably greater than about 0.5% the length L of keel 20. In this embodiment, transition radius $R_{36}$ is about 0.65% of the length L.

Sidewalls 36 each have a thickness $T_{36}$ measured generally parallel to the z-axis, and upper wall 37 has a thickness $T_{37}$ measured generally parallel to the y-axis. In this embodiment, thickness $T_{36}$ of each sidewall 36 is less than thickness $T_{37}$ of upper wall 37. Without being limited by this or any particular theory, for a given material, a reduction in thickness $T_{36}$ and/or thickness $T_{37}$ increases the flexibility of keel body 21 in forefoot portion 30, and an increase in thickness $T_{36}$ and/or thickness $T_{37}$ increases the stiffness of keel body 21 in forefoot portion 30. Accordingly, thickness $T_{36}$ and/or thickness $T_{37}$ may be modified along raised instep 34 to achieve the desired flexibility and stiffness in forefoot portion 30. For a keel body 21 made from polypropylene or a polypropylene-polyethylene blend, thickness $T_{36}$ is preferably about ¼ inch to ⅞ inch, and thickness $T_{37}$ is preferably about ⅜ inch to ¾ inch. More specific dimensions for thickness $T_{37}$ and thickness $T_{36}$ associated with particular embodiments and applications of the prosthetic foot (e.g., prosthetic foot 10) are described in more detail below.

Referring still to FIG. 4, vertical sidewalls 36 and horizontal upper wall 37 of forward raised instep 34 define a recess 35 in the lower surface of forefoot portion 30. Recess 35 has a width $W_{35}$ measured between sidewalls 36 generally parallel to the z-axis, and a depth $D_{35}$ measured between the lower surface of keel body 21 and upper wall 37 generally parallel to the y-axis. Width $W_{35}$ and/or depth $D_{35}$ may be varied along raised instep 34 to adjust the stiffness of forefoot portion 30. In this embodiment, sidewalls 36 taper slightly inward toward each other moving away from ankle portion 40, and thus, width $W_{35}$ decreases moving toward toe end 31. Further, in this embodiment, upper wall 37 and the lower surface of keel body 21 move towards each other moving away from ankle portion 40, and thus, depth $D_{35}$ decreases moving toward toe end 31. For a keel body 21 made of polypropylene or a polypropylene-polyethylene blend, width $W_{35}$ is preferably between about 5% and 15% the overall length L of keel 20 at the intersection with ankle portion 40 and decreases towards toe end 31, and depth $D_{35}$ is preferably between 3% to 10% the overall length L of keel 20 proximal at the intersection with ankle portion 40 and decreases towards toe end 31. In some embodiments, depth $D_{35}$ is varied based on the weight of the patient. For instance, depth $D_{35}$ may be about 9% of the overall length L proximal ankle portion 40 for a relatively heavy patient (e.g., greater than 200 lbs.), about 7% of the overall length L proximal ankle portion 40 for a medium weight patient (e.g., between 100 and 200 lbs.), and about 5% of the overall length L proximal ankle portion 40 for a relatively lightweight patient (e.g., less than 100 lbs).

Referring again to FIGS. 1-3, heel portion 50 includes a base 52 and a raised instep 54. Base 52 has an upturned heel end 51 and a generally concave recess 53 (shown in phantom in FIG. 1). Recess 53 is located on the upper surface of keel body 21 and generally reduces the thickness of keel body 21 within heel portion 50. As a result, recess 13 offers the potential to reduce the weight keel body 21, and increase the flexibility of heel portion 50 by more easily allowing heel portion 50 to bend along its length under loads. Raised instep 54 extends vertically from base 52 generally along longitudinal axis 55 from recess 53 to ankle portion 40.

Figure 5:
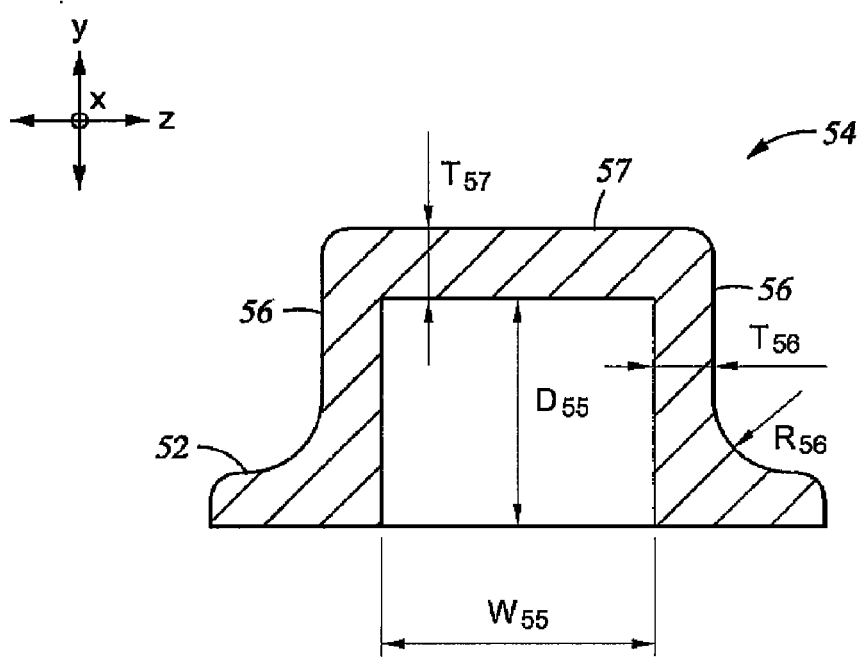
FIG. 5 is a cross-sectional view of the keel of FIG. 1 taken along line C-C of FIG. 2.

Referring now to FIG. 5, a cross-section of keel body 21 in heel portion 50 is shown. Raised instep 54 includes generally vertical sidewalls 56 and a generally horizontal upper wall 57 extending between sidewalls 56. Similar to forefoot portion 30, sidewalls 56 are smoothly blended into base 52 with a transition radius $R_{56}$. To eliminate share edges and the potential for stress concentrations, transition radius $R_{56}$ is preferably greater than about 0.5% the length L of keel 20. In this embodiment, transition radius $R_{56}$ is about 0.65% of the length L.

Sidewalls 56 each have a thickness $T_{56}$ and upper wall 57 has a thickness $T_{57}$. In this embodiment, thickness $T_{56}$ of each sidewall 56 is less than thickness $T_{57}$ of upper wall 57. Without being limited by this or any particular theory, for a given material, a reduction in thickness $T_{56}$ and/or thickness $T_{57}$ increases the flexibility of keel body 21 in heel portion 50, and an increase in thickness $T_{56}$ and/or thickness $T_{57}$ increases the stiffness of keel body 21 in heel portion 50. Accordingly, thickness $T_{56}$ and/or thickness $T_{57}$ may be modified along raised instep 54 to achieve the desired flexibility and stiffness at select locations in heel portion 50. For a keel body 21 made of polypropylene or a polypropylene-polyethylene blend, thickness $T_{56}$ is preferably about ¼ inch to ⅞ inch, and thickness $T_{57}$ is preferably about ⅜ inch to ¼ inch. More specific dimensions for thickness $T_{56}$ and thickness $T_{57}$ associated with particular embodiments and applications of the prosthetic foot (e.g., prosthetic foot 10) are described in more detail below.

Referring still to FIG. 5, vertical sidewalls 56 and horizontal upper wall 57 of raised instep 54 define a recess 55 in the lower surface of heel portion 50. Recess 55 has a width $W_{55}$ measured between sidewalls 56 generally parallel to the z-axis, and a depth $D_{55}$ measured between the lower surface of keel body 21 and upper wall 57 generally parallel to the y-axis. Width $W_{55}$ and/or depth $D_{55}$ may be varied along raised instep 54 to adjust the stiffness of heel portion 50 at select locations in heel portion 50. In this embodiment, sidewalls 56 taper slightly inward toward each other moving away from ankle portion 40, and thus, width $W_{55}$ decreases moving toward heel end 51. Further, in this embodiment, upper wall 57 and the lower surface of keel body 21 move towards each other moving away from ankle portion 40, and thus, depth $D_{55}$ decreases moving toward heel end 51. For a keel body 21 made of polypropylene or a polypropylene-polyethylene blend, width $W_{55}$ is preferably between about 5% and 15% the overall length L of keel 20 at the intersection with ankle portion 40 and decreases towards heel end 51, and depth $D_{55}$ is preferably between 3% to 10% the overall length L of keel 20 at the intersection with ankle portion 40 and decreases towards heel end 51.

Referring again to FIGS. 1-3, ankle portion 40 includes a semi-spherical dome 41, a first bumper capture cavity 42 that receives a first bumper 24, and a second bumper capture cavity 43 that receives a second bumper 25. Dome 41 has a vertically oriented central axis 45 that is substantially parallel with the y-axis and substantially perpendicular to longitudinal axis 25 of keel 20. As best shown in the top view of FIG. 2, in this embodiment, central axis 45, and hence dome 41, is centered relative to ankle portion 40. In other embodiments, the dome (e.g., dome 41) may be positioned off center relative to the ankle portion (e.g., ankle portion 40). Central axis 45 and dome 41 are preferably located between 60% and 80% of the length L of keel 20 from toe end 18, and more preferably between 65% and 75% of the length L of keel 20 from toe end 18. In this embodiment, dome 41 is integral with ankle portion 40 and keel body 21. Consequently, this embodiment advantageously eliminates the need for a separate and distinct rigid dome secured to the keel body with bolts, which may increase the weight of the keel and create stress concentrations in the keel at the bolt locations.

As best shown in FIG. 3, dome 41 also includes an inverted frustoconical counter bore 44, and a bore 48 extending downward from counterbore 44 at least partially through keel body 21. In particular, bore 48 extends generally parallel with the y-axis, and is generally coaxial with central axis 45. In this embodiment, bore 48 does not pass completely through keel body 21, however, in other embodiments, the bore (e.g., bore 48) may pass completely through the keel body (e.g., keel body 21). Counterbore 44 and bore 48 may be formed by any suitable means including, without limitation, machined into keel body 21, molded or cast as part of keel body 21, etc.

Referring still to FIGS. 1-3, a connecting spindle 47 is partially disposed in counterbore 44 and is coupled to keel body 21. Spindle 47 provides a means to couple keel 20, and prosthetic foot 10, to an amputee. For example, the portion of spindle 47 extending above dome 41 may be received and secured by a mating socket mounted on the lower end of a liner worn by the amputee. Consequently, spindle 47 is preferably provided at its upper end with a standard square prosthetic connector, such as an Otto Boch connector or the like.

In order to provide a stable, rigid, and predictable connection between the amputee and keel 20, spindle 47 is preferably rotationally and translationally fixed relative to keel body 21 such that keel 20 and prosthetic foot 10 do not move relative to the amputee, and further, spindle 47 is preferably made from a durable, rigid material such as a metal or a metal alloy such as Grade 5 titanium or 7068 aluminum alloy. In general, the spindle (e.g., spindle 47) may be secured to the keel body (e.g., keel body 21) by any suitable means including without limitation, adhesives, press fitting, pressure fitting, screws, bolts, or combinations thereof. In this embodiment, spindle 47 is secured to keel body 21 with a bolt 49 having a lower end threaded into a T-nutt 46 embedded in ankle portion 40. T-nutt 46 includes a radially extending flange 46a that is surrounded by keel body 21, and thus, is restricted from moving translationally relative to keel body 21. To embed T-nutt 46 within keel body 21 in ankle portion 40 as shown in FIG. 3, T-nutt 46 may be molded as part of keel body 21.

Figure 6:
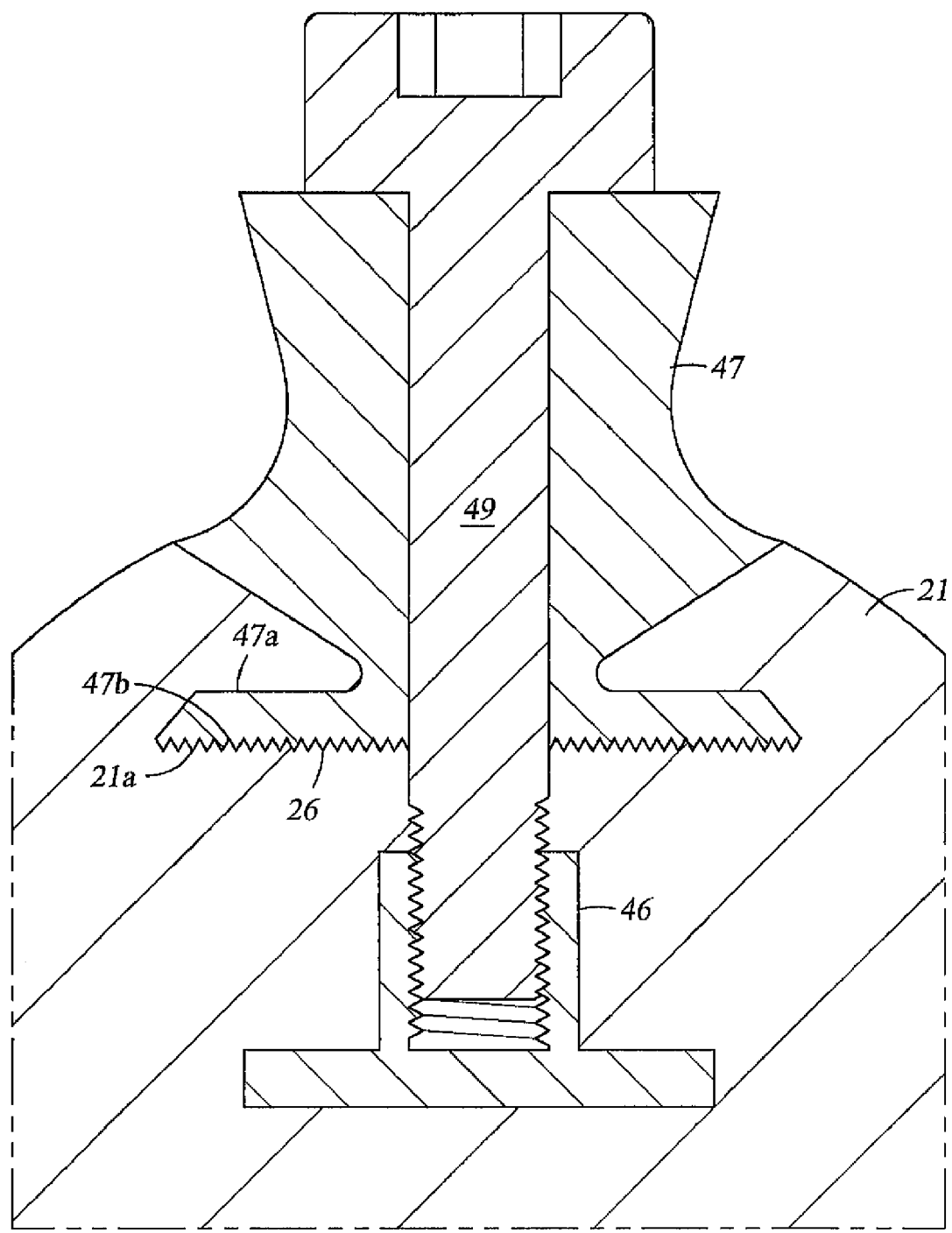
FIG. 6 is an enlarged partial cross-sectional view of the spindle and dome of FIG. 3.

In addition, in this embodiment, the lower end of spindle 47 includes a radially extending flange 47a embedded in ankle portion 40. Flange 47a is surrounded by keel body 21, and thus, is restricted from moving translationally relative to keel body 21. Further, to limit rotational movement of spindle 47 relative to keel body 21, the lower surface of flange 47a is textured to mate and engage with the interfacing surface of keel body 21. As best shown in FIG. 6, in this embodiment, the lower surface of flange 47a comprises a plurality of generally parallel raised ridges 47b that engage mating ridges 21a provided in the interfacing surface of keel body 21. Although parallel, mating raised ridges 47b, 21a are shown in FIG. 6, in general, any suitable mating textured surfaces may be employed including, without limitation, dimples, waffle pattern, etc. To embed flange 47a within keel body 21 in ankle portion 40 as shown in FIG. 3, spindle 47 may be molded as part of keel body 21.

Once spindle 47 is coupled to the amputee, dome 41 bears the majority of the loads (e.g., weight) applied to keel body 21 by an amputee wearing prosthetic foot 10. Dome 41 preferably has relatively smooth surface capable of distributing such applied forces. Without being limited by this or any particular theory, by distributing forces, a relatively smooth surface may reduce or minimize stress concentrations which may otherwise result in premature damage or cracking of keel body 21. Moreover, it should be appreciated that dome 41 has a semi-spherical geometry in this embodiment. The semi-spherical geometry allows for a variety of orientations of prosthetic foot 10 relative to an amputee when prosthetic foot 10 is coupled to the amputee. In particular, the semi-spherical geometry of dome 41 may permit the adjustment of foot 10 about the x-axis, the y-axis, and the z-axis, relative to the amputee. For example, when foot 10 is fitted to an amputee by an Otto Boch connector, the orientation of foot 10 may be adjusted about three axes by varying the position of the female socket of the Otto Boch connector relative to dome 41. Moreover, this feature of dome 41 allows subsequent adjustments of foot 10 about any of the three axes without the need to redesign foot 10.

In the embodiment shown in FIGS. 1-3, dome 41 is integral with keel body 21 and distinct from spindle 47. However, in other embodiments, the dome (e.g., dome 41) may be defined by, and integral with, the spindle (e.g., spindle 47). For instance, referring now to FIG. 7, an embodiment of a keel 20' for a prosthetic foot is shown. Keel 20' is substantially the same as keel 20 previously described. Namely, keel 20' comprises a keel body 21' having an ankle portion 40'. A spindle 47' is coupled to ankle portion 40'. Similar to spindle 47 previously described, spindle 47' has an upper portion adapted to couple keel 20' to the patient. However, in this embodiment, the lower portion of spindle 47' forms a dome 41' that supports substantially all the loads applied by the patient (e.g., weight). Thus, dome 41' is integral with spindle 47', and a separate and distinct component from keel body 21'.

Figure 7:
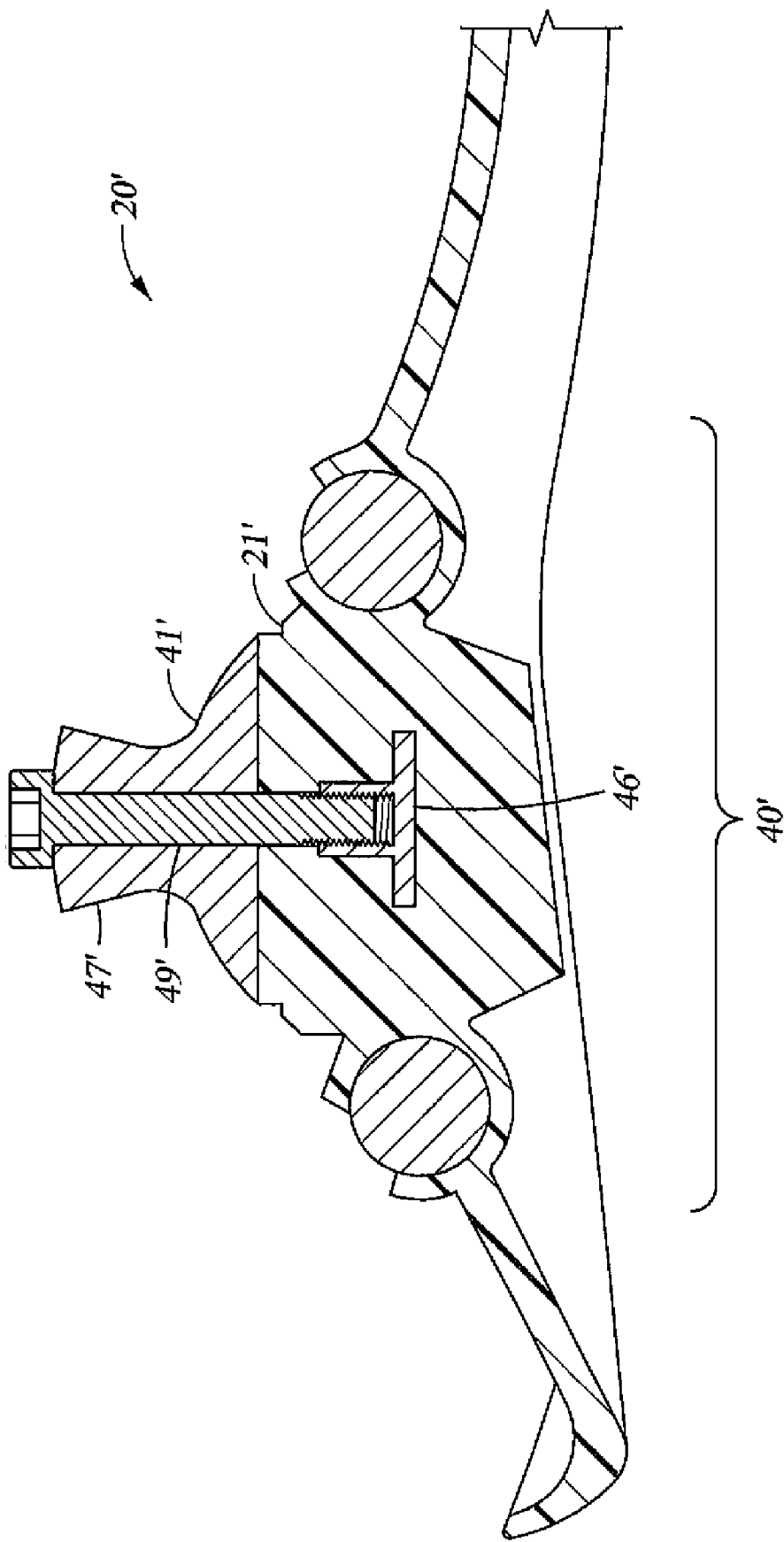
FIG. 7 is an enlarged partial cross-sectional view of an embodiment of a keel made in accordance with the principles described herein.

Referring still to FIG. 7, spindle 47' is translationally fixed relative to keel body 21' with a bolt 49' having a lower end threaded into a T-nutt 46' embedded in ankle portion 40'. The interfacing surfaces of spindle 47' and keel body 21' preferably comprise mating textures that restrict the rotational movement of spindle 47' relative to keel body 21'.

As previously described, the dome (e.g., dome 41, dome 41') bears the majority of the loads (e.g., weight) applied to the keel body (e.g., keel body 21, keel body 21') by the amputee. Consequently, in embodiments where the spindle (e.g. spindle 47') is made from a rigid metal or metal alloy (e.g., grade 5 titanium or 7068 aluminum alloy), it may be preferred that the spindle form the dome, thereby reducing the potential for any deformation of the dome under applied loads.

Referring still to FIGS. 1-3, keel 20 includes bumpers 24, 25 disposed in capture cavities 42, 43. In general, bumpers 24, 25 are employed to simulate the anatomical ankle. To more closely simulate the location, flexion, and feel of the anatomical ankle, the position of each bumper 24, 25 along the longitudinal axis 45 is preferably as close as possible to axis 45, which generally represents that center of the anatomical ankle. However, placement of bumpers 24, 25 through dome 41 or keel body 21 below dome 41 may detrimentally impact the structural integrity and strength of dome 41 and the portion of keel body 21 below dome 41, which tend to bear a bulk of the vertical loads applied by the amputee. Therefore, as best shown in the top view of FIG. 2, in the embodiments described herein, bumpers 24, 25 are disposed along longitudinal axis 25 immediately adjacent dome 41, with bumper 24 just rearward of dome 41 and bumper 25 just forward of dome 41. Although two bumpers 24, 25 are shown in FIGS. 1-3, in other embodiments, fewer or more bumpers may be provided.

Bumpers 24, 25 are preferably secured within capture cavities 42, 43, respectively, such that bumpers 24, 25 are fixed translationally or rotationally relative to keel body 21. To sufficiently retain each bumper 24, 25, more than half of the outer perimeter of each bumper 24, is preferably engaged by cavity 42, 43, respectively. In this embodiment, each capture cavity 42, 43 extends around about 70% to 80% of the perimeter of each bumper 24, 25, respectively. In particular, a pair of opposed retention lips 42a, 43a extend from each capture cavity 42, 43, respectively, around a portion of the outer circumference of each bumper 24, 25, respectively, to sufficiently secure each bumper 24, 25, respectively, therein. Bumpers 24, 25 may be molded into keel body 21 or inserted after keel body 21 has been formed.

In this embodiment, each bumper 24, 25 is cylindrical, has a diameter d, and a central axis 24a, 25a, respectively, oriented substantially perpendicular to longitudinal axis 25 and central axis 45. Consequently, bumpers 24, 25 may also be described as "transverse." In this embodiment, the diameter d of each bumper 24, 25 is substantially the same, however, in other embodiments, the diameter d of each bumper (e.g., bumpers 24, 25) may be different. In other embodiments, one or more of the bumpers (e.g., bumpers 24, 25) may have a non-circular cross-section such as rectangular, triangular, or oval. The inner surfaces of the capture cavities (e.g., capture cavities 42, 43) preferably engage and mate with the outer surfaces of the bumpers (e.g., bumpers 24, 25) such that forces may be directly transferred therebetween. Consequently, in this embodiment, the inner surfaces of capture cavities 42, 43 are cylindrical and engage the outer surfaces of bumpers 24, 25, respectively.

Referring specifically to FIG. 1, cavities 42, 43, and hence bumpers 24, 25 disposed therein, each extend to a depth D measured parallel to the y-axis from the upper surface of keel body 21. Depth D is preferably between 25% and 75% of the height H of ankle portion 40, and more preferably between 35% and 65% of the height H of ankle portion 40. It should be appreciated that the greater the depth D, the lesser the thickness of keel body 21 immediately below cavities 24, 25, thereby tending to increase the flexibility of keel body 21 in such regions. Consequently, the greater the depth D to which cavity 42 and bumper 24 extend, the greater the flexibility and flexion of heel portion 50 relative to ankle portion 40. Likewise, the greater the depth D to which cavity 43 and bumper 25 extend, the greater the flexibility and flexion of forefoot portion 30 relative to ankle portion 40. For example, without being limited by this or any particular theory, positioning bumper 24 at a depth D of about 50% of the height H offers the potential to increase the flexibility of heel portion 50 relative to ankle portion 40 by about 400%.

To more closely simulate an anatomical ankle, each bumper 24, 25 preferably comprises a compressible and resilient material that is softer (i.e., has a lower durometer hardness) than keel body 21. In particular, bumpers 24, 25 are preferably made materials having durometer hardnesses between 60A and 100A. In this embodiment, rear bumper 24 is preferably made from a material having a durometer hardness between 65A and 75A, and more preferably a durometer hardness of about 70A, whereas front bumper 25 is preferably made from a material having a durometer hardness between 75A and 100A, and more preferably a durometer hardness between 80A and 90A. In other embodiments, the bumpers (e.g., bumpers 24, 25) may have the same or similar hardnesses. The materials, and associated durometer hardnesses, of the bumpers (e.g., bumpers 24, 25) may vary depending on a variety of factors including, without limitation, the length L of the keel 20, the expected activities of the amputee, the amputee's age, the desired flexibility, or combinations thereof. Suitable materials for the bumpers (e.g., bumpers 24, 25) include, without limitation, Buta-N rubber and urethane. For a keel body 21 made of polypropylene or polypropylene-polyethylene blend, and bumpers 24, 25 made of a material with a durometer hardness between 60A and 100A (e.g., Buta-N rubber), the diameter d of each bumper 24, 25 is preferably about ¼ inch to ¾ inch, and more preferably about ⅜ inch to ⅝ inch. The diameter d of each bumper 24, 25 is preferably increased as the overall length L of keel 20 increases.

As previously described, bumpers 24, 25 are positioned immediately rearward and forward, respectively, of dome 41 in ankle portion 40 to more closely simulate the location and flexion of the anatomical ankle without detrimentally impacting the structural integrity of dome 41 or the portion of keel body 21 below dome 41. In particular, the compression of bumpers 24, and flexion of the reduced thickness portion of keel body 21 below bumpers 24, 25 allows keel 20 to flex at bumpers 24, 25 in ankle portion 40. It should be appreciated that bumpers 24, are not disposed in forefoot portion 30 nor heel portion 50, and thus, are not designed to enhance the bending or flexion of forefoot portion 30 or heel portion 50. In other words, rear bumper 24 allows heel portion 50 to pivot relative to ankle portion 40 about bumper 24, but has minimal to no impact on the bending of heel portion 50 itself. Likewise, front bumper 25 allows forefoot portion 30 to pivot relative to ankle portion 40 about bumper 25, but has minimal to no impact on the bending of forefoot portion 30 itself. Rather, in the embodiments described herein, the degree of bending of forefoot portion 30 is controlled with the material composition and geometry of forefoot portion 30, and the degree of bending of heel portion 50 is controlled with the material composition and geometry of heel portion 50.

It should be appreciated that ankle portion 40 and bumpers 24, 25, which simulate the anatomical ankle, are integrally part of keel 20. Consequently, embodiments described herein eliminate the need for relatively bulky and heavy distinct ankle prosthetics.

Embodiments of the prosthetic feet and keels described herein may be modified to alter their flexibility and load response depending on particular amputee needs. For assisted walking patients (e.g., patients that require or rely on assistance to occasionally walk), a relatively high flex foot and keel is typically desirable. For such applications, embodiments of prosthetic foot 10 previously described including both a forward bumper 25 and a rearward bumper 24 are preferred; rearward bumper 24 is preferably made from a material with a durometer hardness between 65A and 75A, and more preferably about 70A, and forward bumper 25 is preferably made from a material with a durometer hardness between 80A and 90A inclusive. Further, for such applications, keel body 21 preferably comprises a polypropylene-polyethylene blend that is 4 to 10% polyethylene (by weight), and more preferably a polypropylene-polyethylene blend that is 6 to 8% polyethylene (by weight). Still further, for such applications, sidewalls 36, 56 each preferably have a thickness $T_{36,\ 56}$ between ¼ inch and ⅜ inch, and upper walls 37, 57 each preferably have a thickness $T_{37, 57}$ of about ⅝ inch. Such a design may also be appropriate for certain limited assisted walking patients (e.g., patients that rely on a cane to walk) that desire a more flexible prosthetic.

Figure 8:
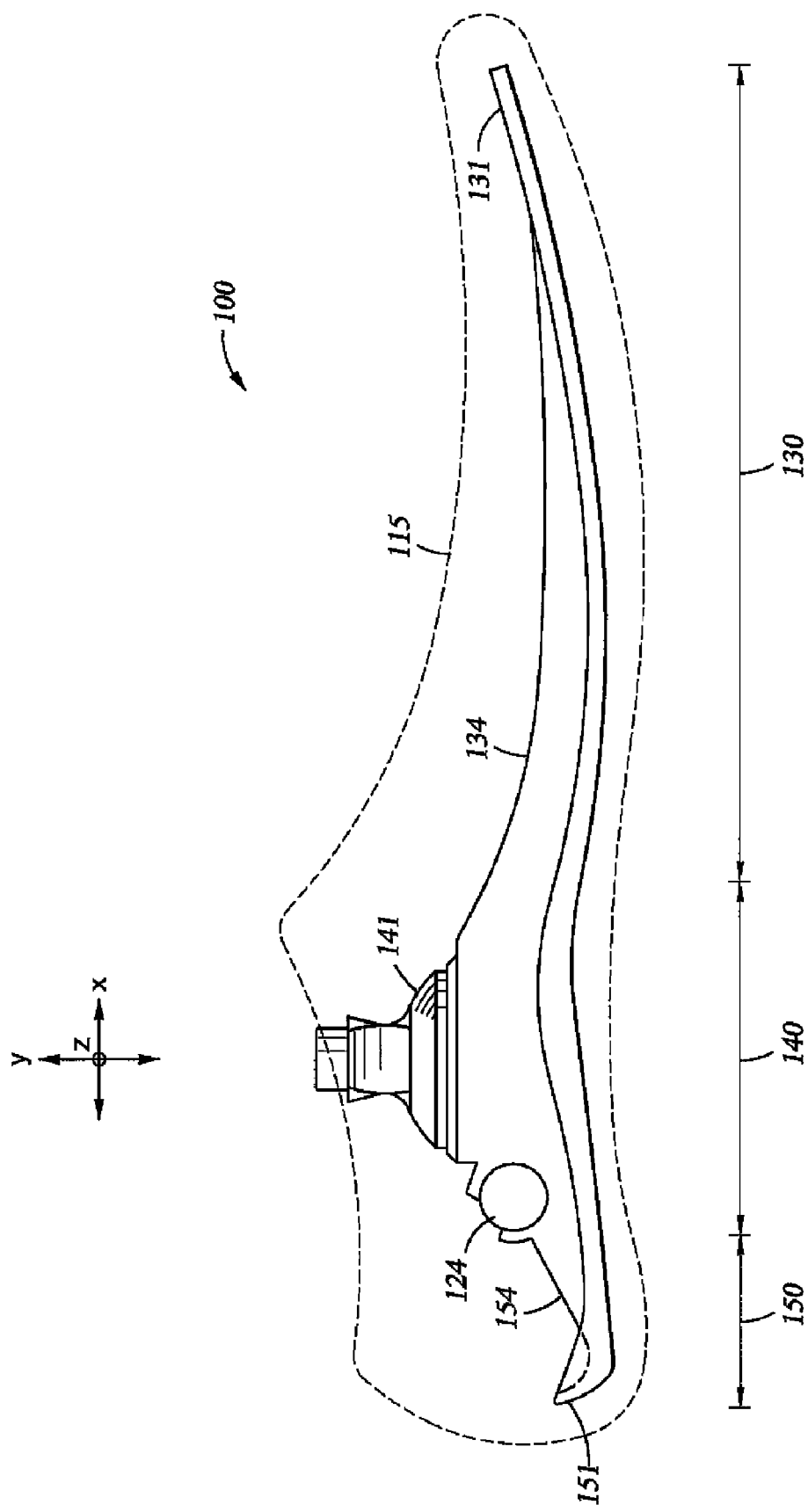
FIG. 8 is a side view of an embodiment of a prosthetic foot made in accordance with the principles described herein.

Referring now to FIG. 8, another embodiment of a prosthetic foot 100 is shown. Prosthetic foot 100 is less flexible than prosthetic foot 10 previously described, and is particularly designed for independent unassisted walking patients (e.g., patients that routinely walk on their own) and select limited assisted walking patients (e.g., patients that rely on a cane to walk). Prosthetic foot 100 is similar to prosthetic foot 10 previously described. Namely, prosthetic foot 100 comprises a keel 120 and a cosmesis 115 (shown in phantom in FIG. 6). Keel 120 comprises a unitary keel body 121 divided into a forefoot portion 130 including a toe end 131 and a raised instep 134, a heel portion 150 including a heel end 151 and raised instep 154, and a ankle portion 140 including a dome 141. However, in this embodiment, keel 120 includes only a single, rear bumper 124 secured to keel body 121 immediately behind dome 141, and thus, generally tends to be less flexible that prosthetic foot 10 including two bumpers 24, 25. Rearward bumper 124 is preferably made from a material with a durometer hardness between 65A and 75A, and more preferably about 70A.

Referring still to FIG. 8, for limited assisted walking patients, keel body 121 preferably comprises a polypropylene-polyethylene blend that is 4 to 10% polyethylene (by weight), and more preferably a polypropylene-polyethylene blend that is 6 to 8% polyethylene (by weight). In addition, for limited assisted walking patients, the sidewalls of each instep 134, 154 preferably has a thickness between ½ inch and ¾ inch, and the upper wall of each instep 134, 154 preferably has a thickness of about ⅝ inch. For independent unassisted walking patients, keel body 121 preferably comprises 100% polypropylene. In addition, for independent unassisted walking patients, the sidewalls of each instep 134, 154 preferably has a thickness between ½ inch and ¾ inch, and the upper wall of each instep 134, 154 preferably has a thickness of about ⅝ inch.

In the manner described, embodiments described herein offer the potential for mechanical improvements over the prior art. Some embodiments have the advantage of providing a relatively lightweight prosthetic foot keel capable of partially simulating the flexion normally provided by an anatomical ankle. In addition, embodiments described herein include an integral semi-spherical dome (e.g., dome 41) allowing for the adjustment of the prosthetic foot (e.g., prosthetic foot 10) about three axes. Further, embodiments described herein offer the potential for a relatively rigid and secure mid-foot (e.g., ankle portion 40) for coupling the prosthetic foot to an amputee without unduly weakening or reducing the flexibility of the keel.

While preferred embodiments of this invention have been shown and described, modifications thereof can be made by one skilled in the art without departing from the scope or teaching of this invention. The embodiments described herein are exemplary only and are not limiting. Many variations and modifications of the system and apparatus are possible and are within the scope of the invention. For example, the relative dimensions of various parts, the materials from which the various parts are made, and other parameters can be varied, so long as the keel 20 device retains the advantages discussed herein. For instance, while the embodiments described above are preferably constructed of fiber composites because of its lightness, strength, flexibility and resiliency, it will be understood that other materials may be equally suitable. Accordingly, the scope of protection is not limited to the embodiments described herein, but is only limited by the claims that follow, the scope of which shall include all equivalents of the subject matter of the claims.

What is claimed is:

1. A keel for a prosthetic foot comprising:
a monolithic keel body having a longitudinal axis and a length L, wherein the keel body includes a forefoot portion, a heel portion, and an ankle portion extending therebetween;
wherein the ankle portion of the keel body includes a first recess defining a first capture cavity;
a first bumper disposed within the first capture cavity, wherein the first bumper has a central axis that is substantially perpendicular to the longitudinal axis of the keel body in top view and an outer perimeter in side view, and wherein the ankle portion extends about and engages a majority of the outer perimeter of the first bumper in side view; and
a spindle extending from the ankle portion of the keel body and adapted to couple the keel body to an amputee, wherein the spindle includes an annular flange embedded in the ankle portion of the keel body;
wherein the first capture cavity is positioned in the ankle portion between the spindle and the heel portion;
wherein the first bumper is cylindrical and has a diameter between ¼ inch and ¾ inch.

2. The keel of claim 1 wherein the monolithic keel body includes a semi-spherical dome extending from the ankle portion, wherein the dome has a substantially vertical centerline located between 65% and 75% of the length L from the toe end.

3. The keel of claim 2 wherein the heel portion has a length measured along the longitudinal axis from a heel end to the ankle portion that is 10% to 20% of the length L, and wherein the ankle portion has a length measured along the longitudinal axis from the heel portion to the forefoot portion that is 8% to 15% of the length L.

4. The keel of claim 2 wherein the keel body is made of a first material having a first hardness, and the first bumper comprises a second material having a second hardness, wherein the first hardness is different than the second hardness.

5. The keel of claim 4 wherein the first material is polypropylene or a polypropylene-polyethylene blend, and the second material comprises a resilient material with a durometer hardness between 65A and 75A.

6. The keel of claim 4 wherein the first bumper is positioned along the longitudinal axis immediately rearward of the semi-spherical dome.

7. The keel of claim 6, wherein the ankle portion of the keel body includes a second recess defining a second capture cavity; and
wherein a second bumper is disposed in the second capture cavity in the ankle portion, wherein the second bumper has a central axis that is substantially perpendicular to the longitudinal axis of the keel body in top view, and wherein the second bumper is disposed along the longitudinal axis immediately forward of the semi-spherical dome.

8. The keel of claim 7 wherein the second bumper is made from a third material having a third hardness, wherein the third hardness is different than the first hardness.

9. The keel of claim 8 wherein the second material and the third material each have a durometer hardness between 60A and 100A.

10. The keel of claim 9 wherein the second material has a durometer hardness between 65 and 75, and the third material has a durometer hardness between 80A and 90A.

11. The keel of claim 10 wherein the first material is polypropylene-polyethylene blend, and the second and third materials are rubber.

12. The keel of claim 10 wherein the second bumper is cylindrical and has a diameter between ¼ inch and ¾ inch.

13. The keel of claim 11 wherein the polypropylene-polyethylene blend is 4 to 10% polyethylene by weight.

14. The keel of claim 13 wherein the polypropylene-polyethylene blend is 6 to 8% polyethylene by weight.

15. The keel of claim 2 wherein the spindle comprises a metal or metal alloy.

16. A prosthetic foot comprising:
a keel;
a cosmesis at least partially disposed about the keel;
wherein the keel includes:
a monolithic keel body having a longitudinal axis and a length L, wherein the keel body includes a forefoot portion having a toe end, an ankle portion including a semi-spherical dome, and a heel portion having a heel end, wherein the ankle portion of the keel body includes a first recess defining a first capture cavity;
wherein the semi-spherical dome defines a portion of an upper surface of the keel; and
a rear bumper disposed within the first capture cavity between the dome and the heel end, wherein the rear bumper has a central axis that is substantially perpendicular to the longitudinal axis of the keel body in top view and a radially outer perimeter;
wherein the keel body extends about and engages a majority of the outer perimeter of the rear bumper in side view;
wherein the rear bumper is cylindrical and has a diameter between ¼ inch and ¾ inch.

17. The prosthetic foot of claim 16 wherein the keel body comprises a first material and the rear bumper comprises a second material that is different from the first material.

18. The prosthetic foot of claim 17 wherein the semi-spherical dome has a centerline substantially perpendicular to the longitudinal axis of the keel body, wherein the centerline is located between 65% and 75% of the length of the keel from the toe end.

19. The prosthetic foot of claim 18, wherein the ankle portion of the keel body includes a second recess defining a second capture cavity; and wherein a front bumper is disposed in the second capture cavity between the dome and the toe end, wherein the front bumper has a central axis that is substantially perpendicular to the longitudinal axis of the keel body in top view.

20. The prosthetic foot of claim 19 wherein the rear bumper is positioned immediately adjacent the dome relative to the longitudinal axis and the front bumper is positioned immediately adjacent the dome relative to the longitudinal axis.

21. The keel of claim 19 wherein the front bumper is cylindrical and has a diameter between ¼ inch and ¾ inch.

22. The keel of claim 18 wherein the keel body comprises polypropylene or a polypropylene-polyethylene blend and each bumper comprises a resilient material having a durometer hardness between 65A and 75A.

* * * * *